United States Patent [19]

Huang

[11] 4,384,161

[45] May 17, 1983

[54] HETEROGENEOUS ISOPARAFFIN/OLEFIN ALKYLATION

[75] Inventor: Tracy J. Huang, Lawrenceville, N.J.

[73] Assignee: Mobil Oil Corporation, New York, N.Y.

[21] Appl. No.: 357,946

[22] Filed: Mar. 15, 1982

[51] Int. Cl.$^3$ .............................................. C07C 2/58
[52] U.S. Cl. ................................ 585/722; 585/331; 585/716; 585/726; 585/727
[58] Field of Search ............... 585/314, 315, 316, 331, 585/715, 716, 717, 719, 722, 726, 727

[56] References Cited

U.S. PATENT DOCUMENTS

| | | | |
|---|---|---|---|
| 3,647,916 | 3/1972 | Caesar et al. | 585/722 |
| 3,655,813 | 4/1972 | Kirsch et al. | 585/722 |
| 3,840,613 | 10/1974 | Eberly, Jr. et al. | 585/722 |
| 3,972,983 | 8/1976 | Ciric | 423/328 |
| 4,021,331 | 5/1977 | Ciric | 208/111 |
| 4,300,015 | 11/1981 | Kirsch et al. | 585/722 |
| 4,331,643 | 5/1982 | Rubin et al. | 423/329 |

*Primary Examiner*—Delbert E. Gantz
*Assistant Examiner*—A. Pal
*Attorney, Agent, or Firm*—Charles A. Huggett; Michael G. Gilman; Charles J. Speciale

[57] ABSTRACT

An improved process for alkylation of isoparaffins with olefins to yield a product which includes a high proportion of highly branched alkylates for blending into gasolines. The improved process comprises contacting the isoparaffins and olefins with a composite catalyst comprising a large pore zeolite and a Lewis acid.

16 Claims, No Drawings

HETEROGENEOUS ISOPARAFFIN/OLEFIN ALKYLATION

BACKGROUND OF THE INVENTION

The present invention relates to the art of improving octane rating of premium gasolines by providing a process for preparing an additive by alkylating an isoparaffin with olefin.

Alkylation is a reaction in which an alkyl group is added to an organic molecule. Thus, an isoparaffin can be reacted with an olefin to provide an isoparaffin of higher molecular weight. Industrially, the concept depends on the reaction of a $C_2$–$C_5$ olefin with isobutane in the presence of an acidic catalyst, producing the so-called alkylate. This is a very valuable ingredient in the manufacture of premium gasolines because of its high octane rating and good response to tetraethyl lead.

Traditionally, processes in the industry include the use of hydrofluoric acid or sulfuric acid and a catalysis carried out under controlled temperature conditions. Low temperatures are required in the sulfuric acid process to minimize the side reaction of olefin polymerization, and the acid strength has to be maintained at 98–100 percent by the continuous addition of fresh acid and the continuous withdrawal of spent acid. The hydrofluoric acid process is less temperature-sensitive and the acid is easily recovered and purified. However, any traces of water in the feedstock must be eliminated owing to the extreme corrosivity of hydrofluoric acid/water solutions.

Although alkylation processes using liquid, acidic catalysts are commercially successful, inherent disadvantages arise, in addition to those mentioned above, in the use of such catalysts including handling and disposal of corrosive materials.

Consequently, substantial efforts have been made to develop a viable isoparaffin-olefin alkylation process using a solid catalyst which is commercially acceptable. For example, U.S. Pat. No. 3,251,902 shows the use of an ion-exchanged crystalline aluminosilicate having a reduced number of available acid sites in fixed bed, liquid phase alkylation of $C_4$–$C_{20}$ branched-chain paraffins with $C_2$–$C_{12}$ olefins, and teaches that the $C_4$–$C_{20}$ branched-chain paraffin should be allowed to substantially saturate the crystalline aluminosilicate before the olefin is introduced to the alkylation reactor. U.S. Pat. No. 3,450,644 discloses a method for regenerating a zeolite catalyst used in hydrocarbon conversion processes involving carbonium ion intermediates. U.S. Pat. No. 3,541,180 discloses a method for improvement of thermal alkylation processes for reacting isobutane with ethylene or propylene which involves using solid sodalite or ultramarine catalysts. U.S. Pat. No. 3,549,557 shows alkylation of isobutane with $C_2$–$C_3$ olefins using certain crystalline aluminosilicate zeolite catalysts in fixed bet, moving bed or fluidized bed systems, with olefin being preferably injected at various points in a fixed bed system. U.S. Pat. No. 3,644,565 discloses alkylation of a paraffin with an olefin in the presence of a catalyst comprising a Group VIII noble metal distended on a crystalline aluminosilicate zeolite, where the catalyst is pretreated with hydrogen to promote selectivity. U.S. Pat. No. 3,647,916 teaches an isoparaffin-olefin alkylation process using an ion-exchanged crystalline aluminosilicate, which includes alkylating at isoparaffin/olefin molar ratios below 3:1 and regenerating the catalyst. U.S. Pat. No. 3,655,813 discloses a process for alkylating $C_4$–$C_5$ isoparaffins with $C_3$–$C_9$ olefins using a crystalline aluminosilicate zeolite catalyst, wherein a halide adjuvant is employed in the alkylation reactor, isoparaffin and olefin are introduced into the alkylation reactor at specified concentrations, and catalyst is continuously regenerated outside the alkylation reactor. U.S. Pat. No. 3,706,814 discloses an isoparaffin-olefin alkylation process, using a crystalline aluminosilicate zeolite catalyst, which includes addition of $C_{5}+$ paraffins "such as Udex raffinate" or $C_{5}+$ olefins to the hydrocarbon feed to the alkylation reactor, and also involves the use of specific reactant proportions, halide adjuvants, etc. Various solid catalysts useful in isoparaffin-olefin alkylation have been disclosed in the above-listed patents and also, for example, in the following. U.S. Pat. No. 3,236,761 discloses the use, in alkylation, of crystalline aluminosilicate zeolites having silica to alumina mole ratios above 3 and also discloses the use of various metals exchanged and/or impregnated on such zeolites. U.S. Pat. No. 3,624,173 discloses the use, in isoparaffin-olefin alkylation, of crystalline aluminosilicate zeolites containing gadolinium. U.S. Pat. No. 3,738,977 discloses alkylation of paraffins with ethylene using a crystalline aluminosilicate with a Group VIII metal distended thereon in which the catalyst has been pretreated with hydrogen. U.S. Pat. No. 3,917,738 shows a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone after which the reactants are passed concurrently with the catalyst so that a controlled amount of olefin is adsorbed onto the catalyst before the combination of reactants and catalyst is introduced into an alkylation zone. This controlled olefin adsorption prevents polymerization of the olefin during alkylation.

Problems arise, however, in the use of solid catalysts in that they appear to age rapidly and cannot perform effectively at high olefin space velocities.

SUMMARY OF THE INVENTION

This invention relates to an improved process of reacting an isoparaffin with olefin molecules in the presence of a composite catalyst comprising a large pore zeolite capable of absorbing 2,2,4-trimethylpentane and a Lewis acid to provide alkylate. The use of a large pore zeolite in combination with a Lewis acid greatly increases the activity and selectivity of the zeolite, thus effecting alkylation with high olefin space velocity and low isoparaffin/olefin ratio.

Zeolites used in the present invention include those which have pores sufficiently large to physically absorb 2,2,4-trimethylpentane, such as, for example, ZSM-4, HZSM-4, ZSM-20, HZSM-20, ZSM-3, HZSM-3, ZSM-18, HZSM-18, ZSM-Beta, faujasite, mordenite, zeolite Y, and the rare earth metal containing form of the above. Additionally, high silica to alumina ratio large pore zeolites can be employed. High framework $SiO_2/Al_2O_3$ ratio may be achieved by processes for dealumining such as steaming, silicon tetrachloride treatment, acid extraction, or by any combination of these methods, or any other means.

A Lewis acid is generally considered to be a molecule which is capable of combining with another molecule or ion by forming a covalent chemical bond with two electrons from the second molecule or ion, that is to say, the Lewis acid is an electron acceptor. Examples of Lewis acids include boron trifluoride, $BF_3$, antimony pentafluoride, $SbF_5$, and aluminum chloride, $AlCl_2$. The present invention contemplates the use of all Lewis acids, such as those set forth in Friedel-Crafts and Related Reactions, Interscience Publishers, Chapters III and IV (1963), which is incorporated by reference.

As a result of the curtailment of the need for octane improving additives, e.g. tetraethyl lead, not only the production of unleaded gasoline has increased, but also the octane number specification of all grades is increased. Isoparaffin-olefin alkylation is a key route to produce highly branched alkylates for blending into gasolines.

EXAMPLES OF THE SPECIFIC EMBODIMENTS

A catalyst composition useful in this invention comprises crystalline aluminosilicate designated ZSM-4, one detailed description of which is found in U.S. Pat. No. 4,021,947, the contents of which are incorporated by reference herein.

ZSM-4 in its aluminosilicate form has the following composition expressed in terms of mole ratios of oxides:

$$0.9 \pm 0.2 \ M_2O:Al_2O_3:3-20 \ SiO_2:0-20 \ H_2O$$

wherein M is selected from the group consisting of a mixture of tetramethylammonium cations and alkali metal cations, especially sodium. ZSM-4 has a distinctive X-ray diffraction pattern which further identifies it from other known zeolites. The original alkali metal cations of ZSM-4 can be exchanged by ion exchange with other ions to form species of the zeolite which have exceptional catalytic properties especially in those hydrocarbon conversion reactions which do not involve any heat transfer.

In accordance with U.S. Pat. No. 4,021,447, there is provided a new form of ZSM-4 having the following formula in terms of mole ratios of oxides:

$$1.0 \pm 0.3 \ R_2O:Al_2O_3:3-20 \ SiO_2$$

on an anhydrous basis wherein R is a mixture of alkali metal cations and nitrogen-containing cations derived from choline salts or pyrrolidone. The original cations can be present so that the amount of nitrogen-containing cations is between 1 and 50 percent of the total amount of original cations. Thus, the zeolite can be expressed by the following, in terms of mole ratios of oxides:

$$1.0 \pm 0.3 [xM_2O + (1-x)R_2O]:Al_2O_3:3-20 \ SiO_2$$

on an anhydrous basis wherein R is derived from choline or salts or pyrrolidone, M is an alkali metal and x is between about 0.10 and about 0.80.

ZSM-4 is prepared by forming a mixture of alumina, silica, sodium oxide, water and tetraethylammonium compounds such that the mixture has a composition, in terms of mole ratios of oxides, falling within the following ranges:

|  | Broad | Preferred | Most Preferred |
|---|---|---|---|
| $\frac{OH^-}{SiO_2}$ | 0.1–1.8 | 0.3–1.6 | 0.3–1.0 |
| $\frac{R_4N^+}{(R_4N^+ + M^+)}$ | 0.01–0.98 | 0.01–0.7 | 0.5–0.7 |
| $\frac{H_2O}{OH^-}$ | 5–300 | 7.5–300 | 10–75 |
| $\frac{SiO_2}{Al_2O_3}$ | 3–60 | 3–60 | 6–30 | wherein $R_4N^+$ is tetramethylammonium cation. The mixture is maintained under conditions of temperatures and pressure until crystals are formed which crystals are separated and recovered.

Members of the family of ZSM-4 zeolites possess a definite distinguishing crystalline structure whose X-ray diffraction pattern has the following values:

TABLE A

| Interplanar Spacing d(A) | Relative Intensity |
|---|---|
| 9.1 ± .2 | VS |
| 7.94 ± .1 | MW |
| 6.90 ± .1 | M |
| 5.97 ± .07 | S |
| 5.50 ± .05 | MW |
| 5.27 ± .05 | MW |
| 4.71 ± .05 | MW |
| 4.39 ± .05 | W |
| 3.96 ± .05 | W |
| 3.80 ± .05 | S |
| 3.71 ± .05 | M |
| 3.63 ± .05 | M |
| 3.52 ± .05 | S |
| 3.44 ± .05 | M |
| 3.16 ± .05 | S |
| 3.09 ± .05 | M |
| 3.04 ± .05 | M |
| 2.98 ± .05 | M |
| 2.92 ± .05 | S |

These values were determined by standard techniques. The radiation was the K-alpha doublet of copper, and a Geiger Counter spectrometer with a strip chart pen recorder was used. The peak heights, I, and the positions as a function of 2 times theta, where theta is the Bragg angle, were read from the spectrometer chart. From these, the relative intensities, $100 \ I/I_o$, where $I_o$ is the intensity of the strongest line or peak, and d(obs.), the interplanar spacing in A, corresponding to the recorded lines, were calculated. In Table A, the relative intensities are given in terms of the symbols VS=very strong, S=strong, M=medium, W=weak and MW=medium weak. It should be understood that this X-ray diffraction pattern is characteristic of all the species of ZSM-4 composition. When the sodium ion is ion exchanged with another cation, X-ray reveals substantially the same pattern with some minor shifts in interplanar spacing and variation in relative intensity. This is also true when the as-synthesized ZSM-4 contains an organic nitrogen-containing ion different from tetramethylammonium.

In a preferred method of preparing a ZSM-4 crystalline aluminosilicate zeolite, the crystallization environment is prepared and into the crystallization environment is introduced a mixture comprising alkali metal, alumina, silica, choline salts or pyrrolidone and water having the following ratios, expressed in terms of mole ratios of oxides:

| | |
|---|---|
| $\dfrac{OH^-}{SiO_2}$ | 0.3–0.82 |
| $\dfrac{R^+}{(R^+ + M^+)}$ | 0.2–0.8 |
| $\dfrac{H_2O}{OH^-}$ | 20–100 |
| $\dfrac{SiO_2}{Al_2O_3}$ | 10–75 | wherein $R^+$ is the ion from choline salts [(2-hydroxyethyl) trimethylammonium salts] or the ion from pyrrolidone and M is alkali metal. The reaction mixture is maintained until crystals of the aluminosilicate are formed. The crystals are separated from the supernatant liquid and recovered. Generally, it is desired to thereafter wash the crystals until the filtrate washings stabilize at a pH below about 11.

This mixture is maintained at reaction conditions until the crystals of the zeolite are formed. Thereafter the crystals are separated from the liquid and recovered. Typical reaction conditions consist of a temperature of from about 75° C. to 175° C. for a period of about 6 hours to 60 days. A more preferred temperature range is from about 90° C. to about 150° C., with the amount of time at a temperature in such range being from about 12 hours to 20 days.

The composition can be prepared utilizing materials which supply the elements of the apropriate oxide. Such compositions include sodium aluminate, alumina, sodium silicate, silica hydrosol, silica gel, silicic acid, sodium hydroxide and the appropriate nitrogen compound. It will be understood that each oxide component utilized in the reaction mixture for preparing ZSM-4 can be supplied by one or more initial reactants and they can be mixed together in any order. For example sodium oxide can be supplied by an aqueous solution of sodium silicate; the organonitrogen cation is supplied by choline salts, e.g. choline chloride, or pyrrolidone. The reaction mixture can be prepared either batchwise or continuously. Crystal size and crystallization time of the ZSM-4 composition will vary with the nature of the reaction mixture employed.

The original metal of most zeolites can be removed by conventional exchange procedures, as by multiple exchanges, i.e. one exchange followed by another. Some zeolites, ZSM-4 included, are not susceptible to this method of exchange, the sodium content reaching a plateau and remaining there regardless of the number of additional exchanges. It has been previously discovered that calcination of the zeolite by removing the tetraethylammonium ion "frees" the sodium so it can thereafter be removed easily. Typical replacing cations include hydrogen, ammonium and metal cations, including mixtures of the same. Of the replacing cations, particular preference is given to cations of hydrogen, ammonium, rare earth, magnesium, zinc, calcium, nickel, and mixtures thereof, generally employed in the form of their salts, preferably the chlorides, nitrates or sulfates. This precalcination is not necessary, although it may still be used to facilitate removal of the sodium cation by means of ion exchange from the products of this invention.

Representative, more detailed ion exchange techniques are disclosed in a wide variety of patents, including U.S. Pat. Nos. 3,410,249, 3,140,251, 3,140,253 and 3,702,886, the contents of which are incorporated by reference herein.

Following contact with the salt solution of the desired replacing cation, the zeolites prepared in accordance with this invention may be washed with water and dried at a temperature ranging from 150° F. to about 600° F. and thereafter may be heated in air or other inert gas at temperatures ranging from about 500° F. to 1500° F. for periods of time ranging from 1 to 48 hours or more. The zeolites thus produced and treated are also useful as cracking catalyst in cracking, hydrocracking, M-forming and dewaxing operation.

It is also possible to treat the zeolite with steam at elevated temperatures ranging from 800° F. to 1600° F. and preferably 1000° F. and 1500° F., if such is desired. The treatment may be accomplished in atmospheres consisting partially or entirely of steam.

A similar treatment can be accomplished at lower temperatures and elevated pressures, e.g. 350°–700° F. at 10 to about 200 atmospheres.

The ZSM-4 produced by the method of this invention may be used in a porous matrix. The zeolites can be combined, dispersed or otherwise intimately admixed with a porous matrix in such proportions that the resulting product contains from 1% to 95% by weight, and preferably from 1 to 70% by weight of the zeolite in the final composite.

The term porous matrix includes inorganic compositions with which the aluminosilicates can be combined, dispersed or otherwise intimately admixed wherein the matrix may be active or inactive. It is to be understood that the porosity of the compositions employed as a matrix can either be inherent in the particular material or it can be introduced by mechanical or chemical means. Inorganic compositions, especially those of a siliceous nature, are preferred. Of these matrices, inorganic oxides such as clay, chemically treated clay, alumina, silica, silica-alumina, etc. are particularly preferred because of their superior porosity, attrition resistance, and stability. More preferably, alumina is the matrix, and it is preferably combined with the zeolite prior to calcination.

Techniques for incorporating the zeolites in a matrix are conventional in the art and are set forth in U.S. Pat. No. 3,140,249, the contents of which are incorporated by reference herein.

The operating temperature of the described alkylation process may extend from −20° to 250° C.; preferably the process is conducted at temperatures from −20° C. to 100° C. The upper operating temperature limits have been found to be determined by the occurrence of undesirable side reactions which reduce the concentration of the reactants.

The pressures employed in the present process may extend over a considerable range, i.e. from about atmospheric to about 5000 psig. Preferably, the pressure is sufficient to maintain at least one of the reactants or reaction products in a liquid phase. Liquid phase operation is believed to promote the length of catalyst activity by preventing the formation of olefinic polymerization and by washing out other by-product high molecular weight compounds from the internal structure of the catalyst caused by the above-mentioned side reactions. Liquid phase operation is considered particularly desirable for alkylation reactions.

The amount of catalyst used in the present process may be varied over relatively wide limits. In general, the amount of catalyst as measured by the liquid hourly space velocity of the olefin may be from about 0.05 to 5. It will be realized that the amount of catalyst selected for a particular reaction will be determined by several variables including the reactants involved as well as the nature of the catalyst and the operating conditions to be used.

In accordance with the process of this invention, the relative molar ratio between the isoparaffin reactant and the olefin alkylating agent is from about 1:1 to about 20:1 and preferably in the range of from about 3:1 to about 10:1.

It will be appreciated that the particular operating conditions employed in the present process will depend on the specific alkylation reaction being effected. Such conditions as temperature, pressure, space velocity and molar ratio of the reactants will have important effects on the overall process. Also the operating conditions for the alkylation reaction in accordance with the process of this invention may be varied so that the same may be conducted in gaseous phase, liquid phase, or mixed liquid-vapor phase, depending upon product distribution, degree of alkylation, as well as the pressures and temperatures at which the alkylation is effected.

The following examples will serve to illustrate the process of the invention without limiting the same.

EXAMPLE 1

Isobutane/butene-2 alkylation was carried out in a 300 ml stainless steel stirred autoclave under pressure using a semi-batch type operation. Seven grams of HZSM-4 were placed in the reactor and 93 grams of isobutane were charged into the reactor under $N_2$ pressure. Then, 6.5 grams of $BF_3$ gas were charged, and the system was stirred at 1800 rpm. After the temperature was raised to 40° C., butene-2 was fed in at a rate of 18.1 grams per hour (2.6 grams of butene-2 per gram of HZSM-4 per hour) for 15 minutes. A total of 4.53 grams of butene-2 was fed into the reactor, and this represented an external isobutane/butene-2 ratio of 20/1. At this time, an on-line sample was taken and analyzed by gas chromatography. The results (Table 1, infra) showed a butene conversion of 97.4% with a $C_5$–$C_{12}$ yield of 1.2 grams $C_5$–$C_{12}$/gram butene converted. The $C_5$–$C_{12}$ fraction contained 92.8 wt.% of $C_8$ paraffins, and the $C_8$ paraffin fraction contained 98.1 mol% of trimethylpentanes. In addition, no olefin in $C_5$–$C_{12}$ was observed.

EXAMPLE 2

The experiment was conducted in the same manner as in Example 1, except that butene-2 was fed in at a rate of 18.1 grams per hour (2.6 butene WHSV) for an hour. This gave an external isobutane/butene ratio of 5/1. The on-line gas chromatography analysis showed a butene conversion of 55.4% with a $C_5$–$C_{12}$ yield of 1.1 grams $C_5$–$C_{12}$ per gram of butene converted. No olefin in $C_5$–$C_{12}$ was observed. The $C_5$–$C_{12}$ product contained 86.1% of $C_8$ paraffins, and the $C_8$ paraffin fraction contained 95.4% trimethylpentanes. The detailed product distribution is given in Table 1, infra.

EXAMPLE 3

The experiment was made in the same manner as in Example 1, except that no $BF_3$ was used. The on-line gas chromatograph analysis indicated that no significant amount of $C_5$–$C_{12}$ was obtained.

EXAMPLE 4

Ten grams of HZSM-4 were placed in the reactor and 70 grams of isobutane were charged into the reactor. Then the system was stirred at 1800 rpm. After a temperature of 100° C. was reached, butene-2 was fed in at a rate of 1.67 grams per hour (0.167 butene WHSV) for 5 hours. At that time, a total of 8.3 grams of butene-2 was fed into the reactor, giving an external isobutane/butene-2 ratio of 8.4/1.0. At the end of the five hour run, the on-line gas chromatograph analysis revealed that butene conversion was 59% and $C_5$–$C_{12}$ yield was 0.94 gram $C_5$—$C_{12}$ per gram of butene converted. The $C_5$–$C_{12}$ product contained 74.8 wt. % $C_8$, and the $C_8$ paraffin fraction contained 87.4 mol % trimethylpentanes. The olefin content in $C_5$–$C_{12}$ was 7.5 wt. %.

TABLE 1

| | ISOBUTANE/BUTENE-2 ALKYLATION | | | |
|---|---|---|---|---|
| EXAMPLE | 1 | 2 | 3 | 4 |
| Catalyst | HZSM-4/$BF_3$ | HZSM-4/$BF_3$ | HZSM-4 | HZSM-4 |
| Temperature, °C. | 40 | 40 | 40 | 100 |
| Pressure, psig | 240 | 240 | 240 | 350 |
| $C_4^=$ WHSV | 2.6 | 2.6 | 2.6 | 0.17 |
| External i-$C_4$/$C_4^=$ | 20/1 | 5/1 | 20/1 | 8.4/1 |
| $C_4^=$ Conversion, % | 97.4 | 55.4 | ↑ | 59.0 |
| $C_5$–$C_{12}$ Yield, (g $C_5$–$C_{12}$/g $C_4^=$ converted) | 1.2 | 1.1 | ↑ ↑ | 0.94 |
| Wt. % of $C_8$ in $C_5$–$C_{12}$ | 92.8 | 86.1 | No | 74.8 |
| $C_5$–$C_{12}$ Distribution, mol % | | | Significant | |
| $C_9^+$ Paraffins | 0.0 | 2.5 | Amount | 7.7 |
| $C_8$ Paraffins | 90.2 | 83.0 | Of | 72.9 |
| $C_7$ Paraffins | 2.2 | 3.3 | $C_5$–$C_{12}$ | 2.8 |
| $C_6$ Paraffins | 2.2 | 4.0 | Was | 4.0 |
| $C_5$ Paraffins | 5.4 | 7.2 | Formed | 5.4 |
| Olefins | 0.0 | 0.0 | ↓ | 7.2 |
| $C_8$ Paraffin Distribution, mol % | | | ↓ | |
| Trimethylpentanes* | 98.1 | 95.4 | ↓ | 87.4 |
| Dimethylhexanes | 1.9 | 4.1 | ↓ | 10.2 |
| Methylheptanes | 0.0 | 0.3 | ↓ | 2.3 |
| n-Octane | 0.0 | 0.2 | | 0.1 |

*Including 2,3-Dimethylhexane

As clearly demonstrated in Examples 1 and 3, HZSM-4 in the presence of $BF_3$, gave enhanced alkylation activity. The comparison between Example 2 and Example 4 shows that the HZSM-4/$BF_3$ system is not only active but also more selective, hence making better alkylate product. Furthermore, much higher olefin space velocity (2.6 $C_4^=$WHSV) with lower i-$C_4/C_4^=$ ratio can be used in the HZSM-4/BF$_3$ system. Higher olefin space velocity means higher production rate. Lower i-$C_4/C_4^=$ ratio means less i-$C_4$ recycle, hence more energy saving.

It is believed that the use of zeolite/Lewis acid catalyst system for isoparaffin/olefin alkylation will eliminate problems associated with conventional liquid acid alkylation. Furthermore, the improved activity and selectivity, together with the more favorable operating conditions such as high olefin space velocity and low isoparaffin/olefin ratio, make the zeolite/Lewis acid catalyst system more economically attractive than zeolite catalyst systems as well as providing an alternative to the conventional HF and H$_2$SO$_4$ alkylation processes.

While there has been provided a description of what are presently believed to be the preferred embodiments of the present invention, other variations and modifications will be recognized by those skilled in the art and it is intended to include all such variations and modifications which lie within the true scope of the present invention which is claimed hereinbelow.

What is claimed is:

1. An alkylation process which comprises effecting reaction of an isoparaffin containing from 4 to 20 carbon atoms with an olefin containing from 2 to 12 carbon atoms at from about $-20°$ C. to about 250° C. and at a pressure in the range of atmospheric to about 5000 psig employing a reaction mixture wherein the molar ratio of said isoparaffin to said olefin is from 2 to 20 in contact with a composite catalyst comprising an large pore zeolite which is capable of absorbing 2,2,4-trimethylpentane and a Lewis acid.

2. The process of claim 1 wherein the isoparaffin contains from 4 to 6 carbon atoms and the olefin contains from 2 to 6 carbon atoms.

3. The process of claim 1 wherein the Lewis acid is selected from the group consisting of BF$_3$, SbF$_5$, and AlCl$_3$.

4. The process of claim 1 wherein the zeolite is selected from the group consisting of ZSM-20, ZSM-3, ZSM-18, ZSM-beta, faujasite, mordenite, zeolite Y, and the rare earth metal containing form of the above.

5. The process of claim 1 wherein the zeolite is HZSM-4.

6. The process of claim 1 wherein the zeolite is a rare earth metal containing HZSM-4.

7. The process of one of claims 1, 3, and 4 wherein the zeolite is contained in a matrix.

8. The process of claim 1 wherein the reaction is conducted under sufficient pressure to maintain at least one of the reactants in a liquid phase.

9. The process of claim 1 wherein the molar ratio of the isoparaffin to the olefin is from 3 to 10.

10. The process of claim 1 wherein the isoparaffin is isobutane and the olefin is butene.

11. The process of claim 10 wherein the zeolite is selected from the group consisting of ZSM-4, ZSM-20, ZSM,-3, ZSM-18, ZSM-beta, faujasite, mordenite, zeolite Y, and a rare earth metal containing form of the above.

12. The process of claim 10 wherein the zeolite is HZSM-4.

13. The process of claim 10 wherein the zeolite is HZSM-20.

14. The process of claim 10 wherein the zeolite is a rare earth metal containing HZSM-4.

15. The process of claim 10 wherein the zeolite is a rare earth metal containing HZSM-20.

16. The process of claim 1 wherein the zeolite is dealuminized by steaming.

* * * * *